United States Patent [19]
Yeh

[11] Patent Number: 5,465,445
[45] Date of Patent: Nov. 14, 1995

[54] HYDRAULICALLY OPERATED TOOTHBRUSH

[76] Inventor: Richard T. Yeh, 13572 Montague St., Arleta, Calif. 91331

[21] Appl. No.: 237,861

[22] Filed: May 4, 1994

[51] Int. Cl.$^6$ .......................... A61C 17/30; A46B 13/06
[52] U.S. Cl. ............................................................. 15/29
[58] Field of Search ............................. 15/28, 29, 22.1, 15/24

[56] References Cited

U.S. PATENT DOCUMENTS

| | | | |
|---|---|---|---|
| 3,869,746 | 3/1975 | Man-king | 15/29 |
| 4,274,173 | 6/1981 | Cohen | 15/29 |

Primary Examiner—Edward L. Roberts, Jr.
Attorney, Agent, or Firm—Paul Adams

[57] ABSTRACT

A hydraulically operated toothbrush in which the flow of water from a faucet through the toothbrush handle and into the head produces rotation of a plurality of bristles mounted in the head, the bristles also being mounted for limited axially movement, and including a device for regulating the water pressure within the head to thereby assure the proper rotation of the bristles. The toothbrush may also include a siphoning tube operated by the suction created when water passes into the toothbrush, one end of the tube being inserted into the user's mouth and the other in a discharge basin. The siphoning tube may also be fitted with a mouth rinse fluid cup to introduce small amounts of fluid into the user's mouth during the brushing.

11 Claims, 4 Drawing Sheets

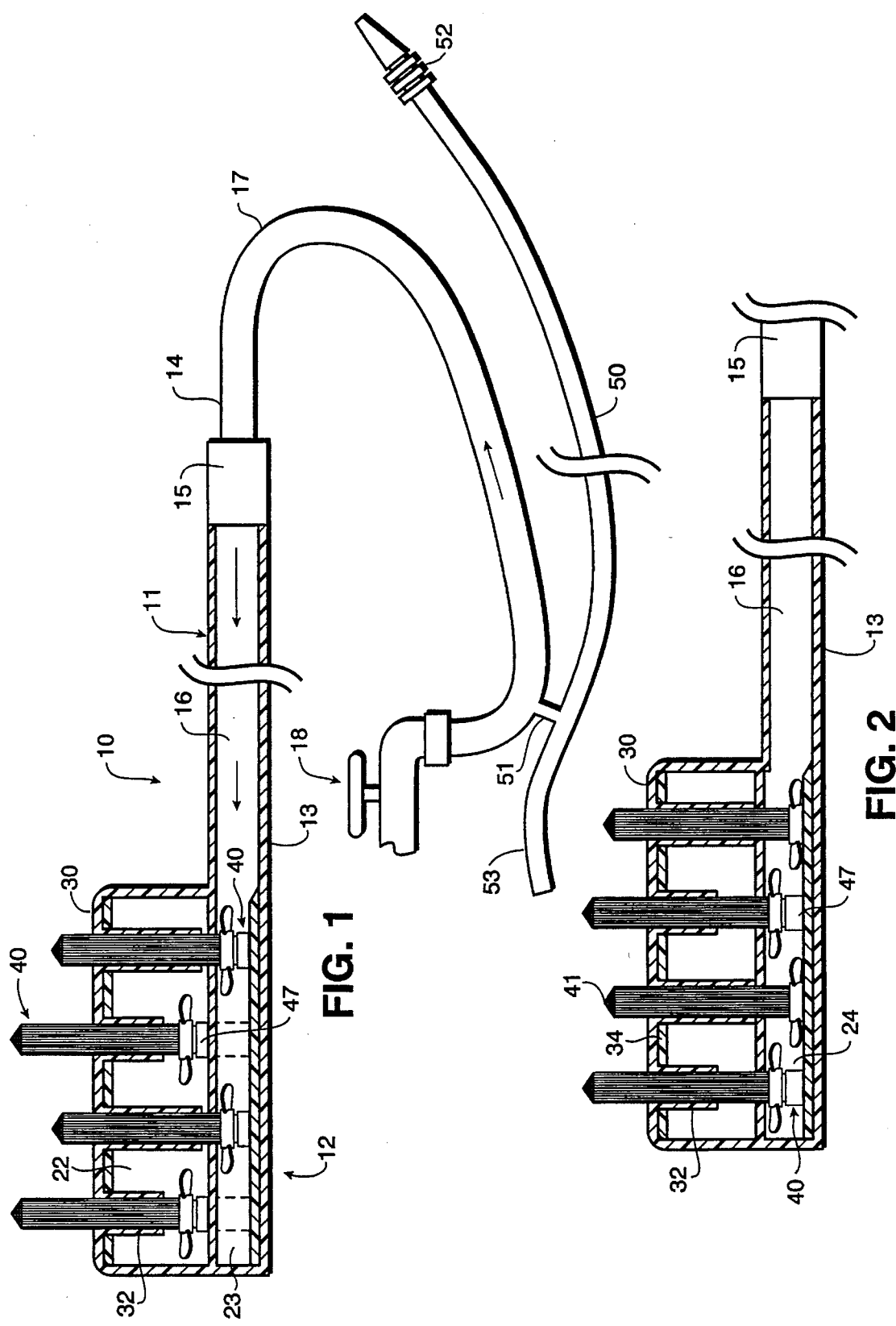

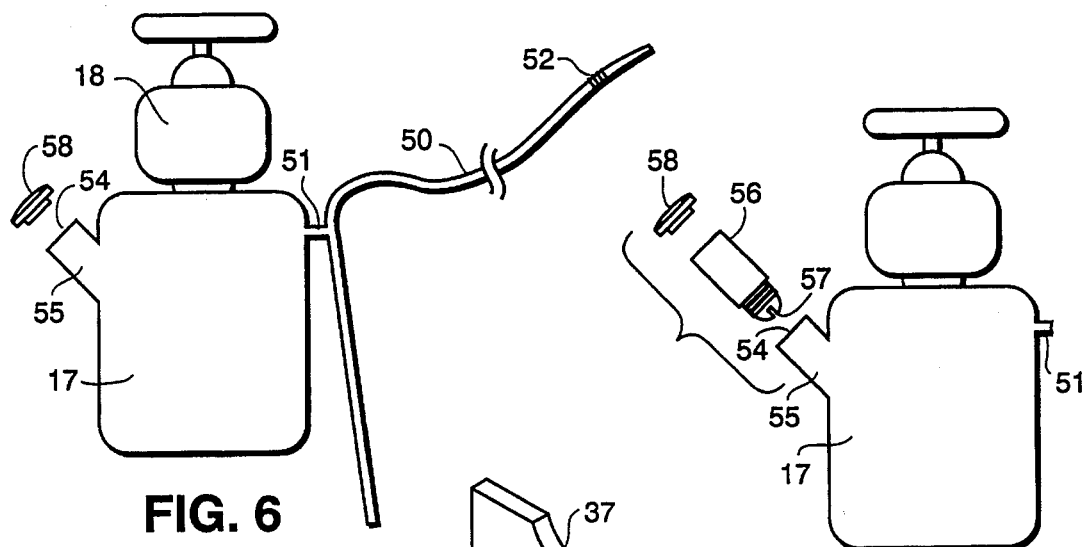
FIG. 6
FIG. 6A
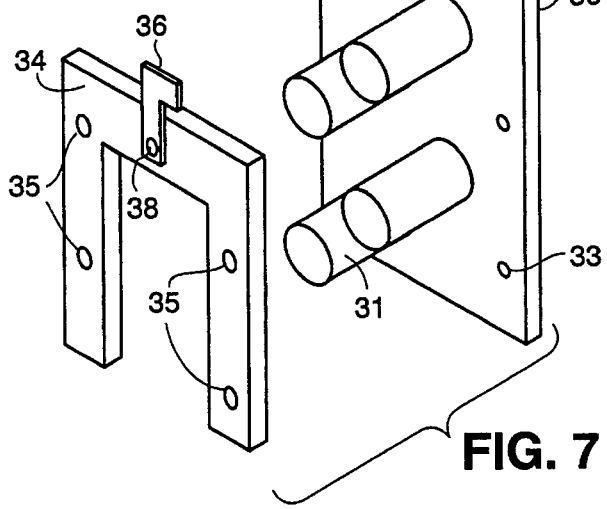
FIG. 7
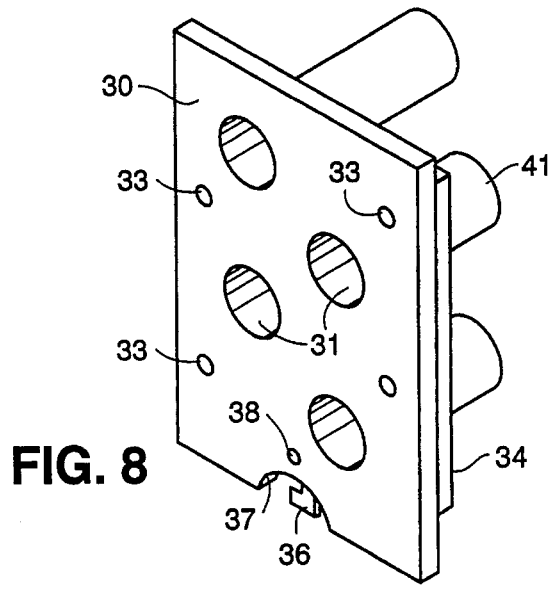
FIG. 8

HYDRAULICALLY OPERATED TOOTHBRUSH

This invention relates to a hydraulically operated toothbrush in which water pressure is used to rotate and move the bristles on the head of the brush so as to improve the tooth and gum cleansing action.

PRIOR ART

It is known in the prior art to employ the hydraulic pressure of water from a source such as a water faucet to rotate bristles on the head of a toothbrush. An example of this type of hydraulic toothbrush is shown in U.S. Pat. No. 3,869,746.

However, there are certain limitations to hydraulic toothbrushes shown in the prior art. One such limitation relates to the operability of the toothbrush as shown in the above-mentioned patent because of the lack of pressure differential between the water source and the cavity in which the propellers attached to the bristles are mounted. Another disadvantage of this prior art toothbrush is that the bristles all end in the same plane which does not permit the effective positioning of the bristles between the teeth to fully cleanse the teeth.

SUMMARY OF THE INVENTION

It is therefore a broad object of this invention to provide a hydraulically operated toothbrush that has highly effective bristle rotating action to properly cleanse the user's teeth and gums.

Another object is to provide such a toothbrush additionally having axial or lateral movement of the bristles simultaneously with the rotating action. One more object is to carry out the broad object stated above by assuring a pressure differential between the water source and the water within the cavity of the toothbrush head where the rotating action of the bristles is effected through a propeller-like mechanism.

It is still another object of the invention to further the convenience in using the toothbrush through the provision of a siphoning tube that will suck water discharged from the toothbrush head through the tube and into a suitable waste receptacle.

Yet another object of the invention is to introduce mouth rinse fluid into the flow of high pressure water into the toothbrush and the user's mouth so as to allow a simultaneous rinsing and cleansing of the mouth.

In summary, the invention shows a hydraulically operated toothbrush including an elongated handle with a water passage therethrough adapted to be connected to a high pressure source of water such as a faucet, a head at one end of the handle with a cavity therein and having one or more water channels connected to the water passage and openings in each channel into the cavity, the head also including openings for receiving bristles that extend into the cavity, and means for rotating the bristles attached to the bristles within the cavity so that the high pressure water emanating from the openings in the channels cause the bristles to rotate. The invention may also include a construction of the head openings that allows the bristles to move axially, that is inward and outward with respect to the head, and the rotating means comprises a propeller that produces an axial thrust when the water impinges on the propeller blades producing simultaneous rotation and lateral movement. The invention also may include a siphoning tube for insertion into the user's mouth to remove the water discharged from the toothbrush. It may also include a mouth rinse cup and fluid in the siphoning tube to introduce mouth freshener into the user's mouth during brushing.

The foregoing and other objects of the invention will become apparent from the more particular description of a preferred embodiment of the invention as illustrated in the accompanying drawings.

BRIEF DESCRIPTION OF THE DRAWING

FIG. 1 is sectional side view of a toothbrush constructed in accordance with the present invention including the siphoning tube and showing the bristle means in an extended position;

FIG. 2 is a view similar to FIG. 1 showing the bristle means in a rest position;

FIG. 6 an enlarged view of the siphoning tube and the mouth rinse fluid cup; FIG. 6A shows the mouth rinse fluid cup disassembled;

FIG. 7 shows the plate and a portion of the underside of the top wall of the toothbrush head for adjusting flow control out of the cavity of the toothbrush head; and FIG. 8 shows the upper wall of the toothbrush head and the closing plate.

DESCRIPTION OF THE PREFERRED EMBODIMENT

Figure 3:
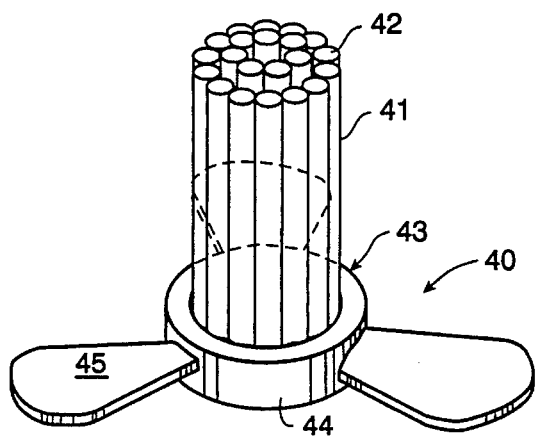
FIG. 3 is an enlarged detail view of the bristle means.

Referring now to FIG. 1, there is shown a hydraulically operated, movable bristle toothbrush 10 comprising a handle assembly 11, and a head 12. The toothbrush 10 may be constructed of various materials and using various manufacturing methods including plastic material that is injection molded.

The handle assembly 11 comprises a forward portion 13 and an end portion 14 which may be detachable through, for example, a threaded fitting 15. The t forward and end portions of the handle, 13 and 14, include a water passage 16. The end portion 14 of the handle, as shown in this embodiment, has a detachable flexible tube 17 for connecting the water passage 16 to a water faucet or nozzle 18 or other source of high pressure water. For purposes of regulating the flow and pressure of the water through the water passage of the toothbrush 10, the faucet 18 may be hand adjusted. The fitting 15 joining the forward and end portions of the handle 11 comprises male and female threaded members.

Figure 5:
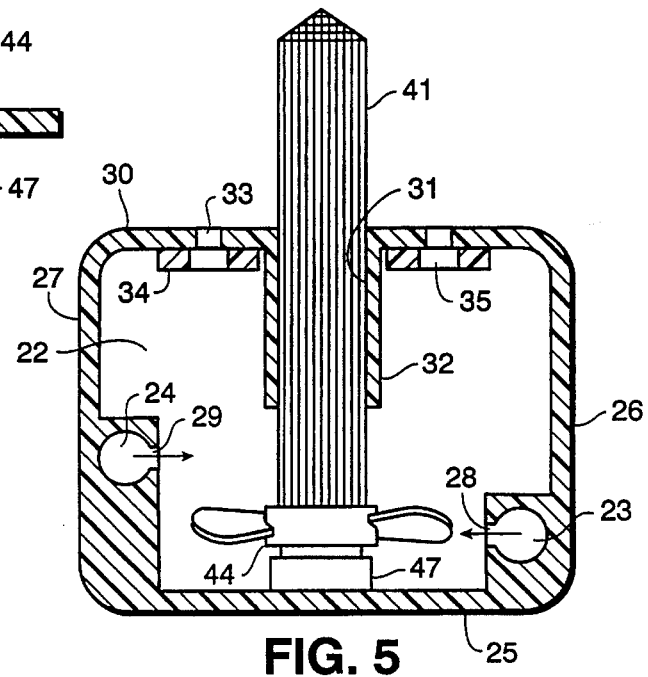
FIG. 5 is a sectional view of the head construction.
Figure 4:
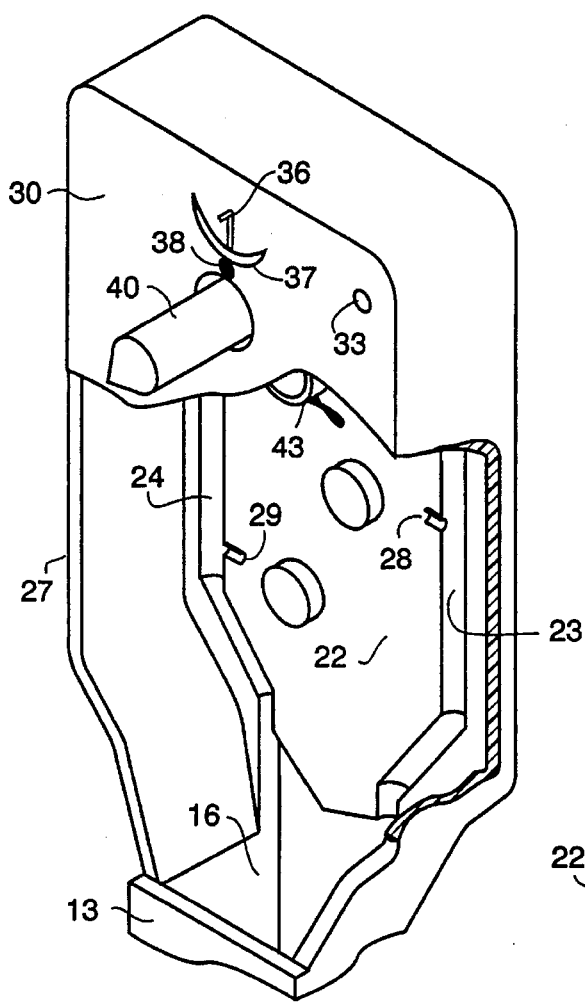
FIG. 4 and 4A show the head construction of the hydraulic toothbrush.
Figure 4A:
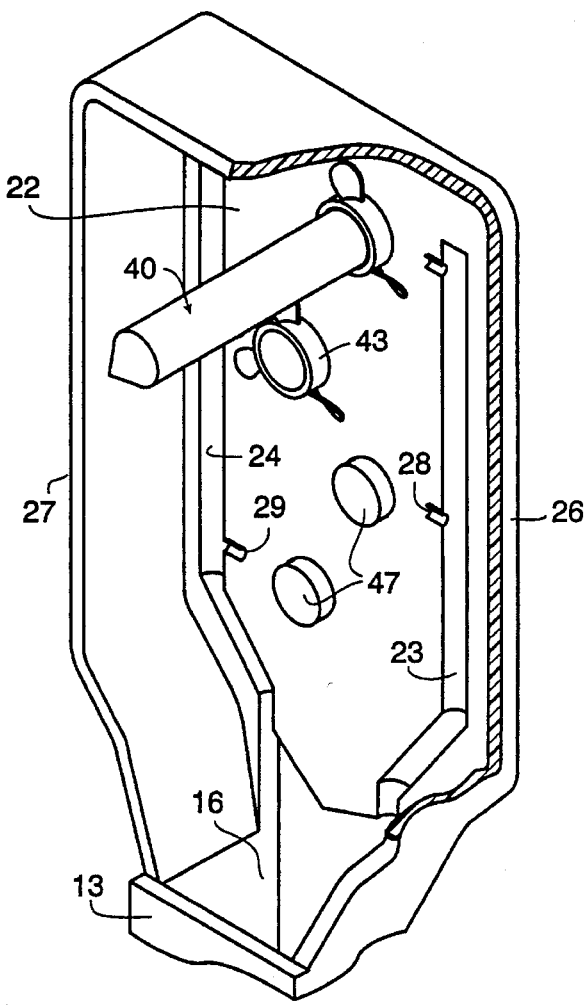

Referring now to FIGS. 4, 4A, and 5 in addition to FIGS. 1 and 2, the head 12 includes a cavity 22 which contain a plurality of bristle means 40 described more fully below. In this embodiment, there is shown two parallel, elongated water channels 23 and 24 in fluid communication with the water passage 16 in the handle. As seen best in FIG. 5, the water channels 23 and 24 are in two different horizontal planes, the channel 23 being lower, that is, closer to the bottom wall 25 of the head while the channel 24 is positioned generally in the central portion of the cavity 22. The bottom wall 25 together with the side walls 26 and 27 and top wall 30, as seen best in FIG. 4, define the cavity 22. The channels 23 and 24 extending longitudinally near the side walls 26 and 27 of the head have one or more fluid openings into the cavity 22. In the embodiment shown, the channels 23 and 24 have a restricted flow cross section relative to the water passage 16. Openings, such as the opening 28 for channel 23, and opening 29 for channel 24 provide fluid communication between the longitudinally extending channels and the cavity so as to discharge water at high pressure into the cavity. The openings 28 and 29 each have a reduced flow cross-section, compared to water channels 23 and 24 and the aggregate cross-sectional area of all openings, are less than the aggregate cross-sectional areas of the two channels 23 and 24.

Figure 3A:
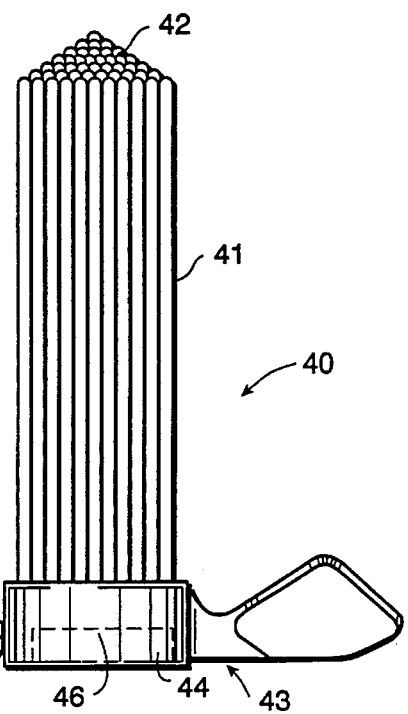
FIG. 3A is a side view of the bristle means.
Figure 3B:
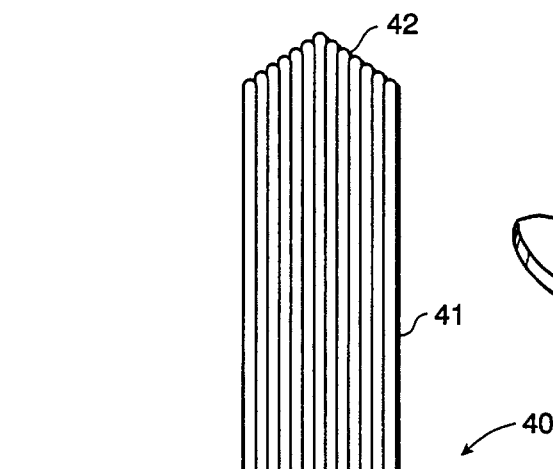
FIG. 3B is a sectional view through the propeller portion of the bristle means.

The top wall 30 of the head includes a plurality of openings such as opening 31 shown in FIG. 5, for accepting a bristle. In the preferred embodiment, a row of such openings, as shown in FIGS. 1 and 2, is provided for a plurality of bristles. Aligned with each opening 31 is a downwardly extending hub or collar 32 which may be integrally formed with the top wall 30. Also formed in the top wall 30 is a plurality of discharge openings 33 of substantially smaller diameter than the openings 31 for the bristles. The discharge openings 33 may be formed adjacent the bristle openings, but the number of such openings rather than their position being more important for proper operation of the hydraulic toothbrush. As seen in FIGS. 7 and 8, beneath the top wall 30, i.e. within the cavity 22, there is provided means for opening and closing, partially or fully, the discharge openings 33 in the top wall 30. In this embodiment, the closing means comprises a U-shape plate 34, having a plurality of openings 35, of the approximately same diameter as the openings 33 in top wall 30. At the forward end of the U-shaped plate 34 is small tab 36 which is exposed through an aperture 37 in top wall 30. The plate 34 is pivotally mounted to top wall 30 through pin 38. The bristle means 40, shown in detail in FIGS. 3, 3A, and 3B may comprise a plurality of fine, hair-like members that are tightly bound into a single bristle 41 or may be a single member. In the preferred embodiment, the free end of the bristle 41 may be formed into a cone 42. At the lower end of each of the bristles 41 is a propeller 43 having a hub 44 and a plurality of blades 45. The lower end of the hub 44 may be provided with an opening 46 for receiving the upper end of a guide member 47 attached to the bottom wall 25 of the head. As will be seen, all of the bristles have the same length, however as seen best in FIG. 1, the members 47 may be of different heights so that in their rest position the upper end of the bristles 41 are alternatingly at different heights. As seen best in FIG. 5, showing one of the lower positioned bristle means, the blades 45 of the bristle means 40 are in the same plane as the opening 28 of channel 23 whereas the opening 29 of channel 24 on the opposite side of the cavity 22 is in a different plane, one that is co-planar with the blades 45 on another of the bristle means.

In FIG. 1 it will be seen that the flexible tube 17 may have attached to it a siphoning tube 50 through a small orifice 51 that provides fluid communication between the flexible tube 17 and the siphoning tube 50. One end of the siphoning tube at 52 is for insertion into the mouth of the user of the toothbrush and the other end 53 is for insertion into a waste receptacle.

As seen in FIG. 6 and 6A, the flexible tube 17 may be provided with an opening 54 in a branching stub tube 55. A small cup 56 with an opening 57 for containing mouth rinse fluid may be inserted through the opening 54 into the stub 55 which may then be closed with a cover 58.

To operate the hydraulic toothbrush 10, the flexible tube 17 is attached to the free end of a water faucet 18 which is opened to admit a flow of water through the tube 17 into the water passage 16 of the handle 11 and through the channels 23 and 24 so as to discharge through orifices 28 and 29 on the blades 45 of each of the bristle means 40 producing a rotation of the bristle 41 to effect a cleansing action on the users teeth and gums. Through the action of the water on the propeller blades, the blades will also produce an upward thrust so that the bristles 41, shown at rest in FIG. 2, are driven outward and against the surface of the tooth or gum, as seen in FIG. 1. Through the application of pressure by the user of the toothbrush, the bristles are forced against the teeth and gums. In the course of brushing, the bristles will be forced outwardly (axially) by the water, then inwardly due to the user's pressure, and this continuous action produces a constant motion of the bristles, in and out, during the simultaneous rotation thereby increasing the cleansing action.

In order to rotate the propeller means, the pressure of the water emanating from the channel openings, such as at 28 and 29, must be greater than the pressure of the water within the cavity 22. The user can determine whether the necessary pressure differential exists by observing if the bristles 41 are rotating. If not, or to increase the rotation at a greater rate of speed, the user may move tab 36 on the plate 34 so as to adjustably move the plate 34 to thereby partially or fully open the discharge openings 33 in the top wall 30 of the toothbrush head. This movement will relieve the pressure within the cavity assuring that the bristles rotate properly. In order to use the water discharge from the openings 33 as a high pressure cleansing jet, the openings 33 may be partially closed thereby increasing the force of the water discharged through such openings 33. This will assist in the cleansing action of the toothbrush.

The user may elect to withdraw excess water from the user's mouth by inserting the end 52 of the siphoning tube 50 while simultaneously placing the other end 53 into a discharge vessel such as a wash basin. As the water flows through flexible tube 17 and past the orifice 51, it will create a vacuum in the siphoning tube 50 to thereby suck the water from the user's mouth and discharge it into the wash basin. This action is enhanced by the fact that in ordinary usage the toothbrush and the users mouth is located above the plane of the free end 53 within the wash basin; thus, the force of gravity will assist in the siphoning action.

As an additional option in the use of the hydraulically operated toothbrush, mouth rinse fluid may be injected into the water flow through the toothbrush and into the user's mouth by filling the cup 56 with a mouth rinse fluid so that the flow of water through the tube 17 will draw small amounts of the mouth rinse fluid into the water flowing through the toothbrush. In this manner the user can effect simultaneous brushing and rinsing.

Although the description above specifically describes many of the elements of the invention with great particularity, this should be understood as a presentation of the invention in one single embodiment, which should not be understood as limiting the scope of the invention. For example, the head of the toothbrush may be molded in a single piece including the channels and the handle; there are various ways of opening and closing the discharge openings in the top wall of the head to regulate the pressure within the cavity to assure vigorous rotation of the bristles, and different configurations and shapes of propellers or other means for converting the high pressure water coming into the cavity into a rotating motion of the bristles. Accordingly, the scope of the invention should be determined by the appended claims.

What is claimed is:

1. A hydraulically operated movable bristle toothbrush comprising:

(a) an elongated handle having a longitudinal water passage, said passage being connectable to a pressurized water source;

(b) a head formed at one end of said handle having a main cavity and at least one channel with a flow cross-section smaller than said handle water passage, said channel having at least one opening into said cavity, said head having a plurality of openings for accepting bristles and a plurality of discharge openings; and (c) a plurality of bristle means rotatably mounted in said cavity, each said bristle means including a cylindrical bristle projecting laterally through and rotatably mounted in one of said bristle openings and including a propeller, means, said propeller means including propeller blades fixedly mounted to the portion of the bristle within the cavity whereby water discharged at high pressure from said channel against the propeller blades will rotate the bristle to effect a cleaning action.

2. The hydraulically operated movable toothbrush of claim 1 wherein said bristles are axially movable in said openings and said propeller has a blade angle producing an axial thrust in addition to rotation causing said bristles to be partially driven out of said cavity against the tooth or gum surface so as to increase the cleansing action.

3. The hydraulically operated movable toothbrush of claim 1 additionally including adjustable closing means movably mounted in said cavity for selectively partially or fully opening and closing said discharge openings to regulate the pressure within said cavity to assure a pressure differential between the channel water and the cavity water and to increase the force of the water discharged through said openings to effect a cleansing stream of water against the teeth and gums.

4. The hydraulically operated movable toothbrush of claim 1 wherein each of said bristles comprises a plurality of hair-like elements that are tightly bundled.

5. The hydraulically operated movable toothbrush of claim 1 having at least two channels in said head, said channels being in different planes, each of said bristle means having bristles of the same length, said bristle means disposed in a row along the longitudinal axis of said head, and alternating bristle means being mounted at different heights, one set of said bristle means having its propellers in the plane of one of said channels and the other set of bristles having its propellers in the plane of the other channel.

6. The hydraulically operated movable toothbrush of claim 1 additionally including a siphoning tube with an orifice opening to the water passage of said handle, one end of said tube being insertable into the mouth and the other end being deposited in a waste receptacle, whereby the movement of the water in the passage causes a suction in said tube to thereby remove water from the mouth and deposit it in the receptacle.

7. The hydraulically operated movable toothbrush of claim 1 wherein said handle has a flexible tube extension for attachment to a water faucet.

8. The hydraulically operated movable toothbrush of claim 7 wherein said flexible tube and a portion of said handle may be disconnected from the toothbrush.

9. The hydraulically operated movable toothbrush of claim 1 wherein said flexible tube includes a branching tube stub and additionally including a mouth rinse fluid cup insertable into said stub, said cup having an opening allowing a portion of the rinse fluid to be drawn into the flow of water passing from the water source into the toothbrush.

10. A hydraulically operated movable bristle toothbrush comprising:

(a) an elongated handle having a longitudinal water passage and a flexible tube connectable to a pressurized water source;

(b) a head formed at one end of said handle having a main cavity defined by a bottom wall, four side walls including two elongated walls and front and rear walls, and a top wall, a pair of channels adjacent the two elongated side walls, each of said channels having at least one opening into said cavity, the top wall having one or more rows of openings for accepting bristles and a plurality of discharge openings for permitting the water entering the head to be discharged out of the toothbrush;

(c) a closing member mounted within said cavity for selectively opening and closing of the discharge openings to thereby regulate the pressure in the cavity so as to maintain the cavity pressure less than the entry water pressure; and (d) a plurality of bristles, each bristle rotatably mounted in said cavity and projecting laterally through and rotatably mounted in one of said top wall openings and propellers, each propeller fixedly mounted to the portion of one of said bristles within the cavity whereby water discharged at high pressure from said channels against the propeller blades rotate the bristles to effect a cleaning action.

11. A hydraulic toothbrush comprising:

(a) an elongated handle having a longitudinal water passage and a flexible tube connectable to a water faucet;

(b) a head mounted at one end of said handle including a bottom wall, four side walls including two elongated walls and front and rear walls, and a top wall to thereby define a cavity, and at least one channel connecting the water passage and the cavity, the top wall having one or more rows of openings for accepting bristles and a plurality of discharge openings for permitting the water entering the head to be discharged out of the toothbrush;

(c) a plurality of bristle means rotatably mounted in said cavity and projecting laterally through and rotatably mounted in one of said top wall openings and means for rotating said bristles mounted to the portion of each of said bristles within the cavity whereby water discharged at high pressure from said channel rotates the bristles to effect a cleaning action; and (d) a siphoning tube with an orifice opening to the water passage of said handle, one end of said tube being insertable into the mouth and the other end being deposited in a waste receptacle, whereby the movement of the water in the passage causes a suction in said tube to thereby remove water from the mouth and deposit it in the receptacle.

* * * * *